United States Patent [19]

Cragoe, Jr. et al.

[11] 4,115,573

[45] Sep. 19, 1978

[54] N-PYRAZINECARBONYL-N'-SUBSTITUTED-SULFAMOYLGUANIDINE AND PROCESSES FOR PREPARING SAME

[75] Inventors: Edward J. Cragoe, Jr., Lansdale; Otto W. Woltersdorf, Jr., Chalfont, both of Pa.

[73] Assignee: Merck & Co., Inc., Rahway, N.J.

[21] Appl. No.: 774,360

[22] Filed: Mar. 4, 1977

[51] Int. Cl.² .................. A61K 31/495; C07D 241/02
[52] U.S. Cl. ..................................... 424/250; 544/407
[58] Field of Search .................. 260/250 BN; 424/250

[56] References Cited

U.S. PATENT DOCUMENTS

| 2,542,856 | 2/1951 | Wright et al. | 260/250 BN |
| 3,240,780 | 3/1966 | Cragoe et al. | 260/250 BN |
| 3,573,305 | 3/1971 | Cragoe et al. | 260/250 BN |
| 3,833,578 | 9/1974 | Ambrogi et al. | 260/250 BN |

Primary Examiner—Donald G. Daus
Assistant Examiner—James H. Turnipseed
Attorney, Agent, or Firm—Michael C. Sudol, Jr.

[57] ABSTRACT

The case involves novel N-pyrazinecarbonyl-N'-substituted-sulfamoylguanidine and processes for preparing same. The N-pyrazinecarbonyl-N'-substituted-sulfamoylguanidines are excellent eukalemic agents possessing diuretic and natriuretic properties.

5 Claims, No Drawings

N-PYRAZINECARBONYL-N'-SUBSTITUTED-SULFAMOYLGUANIDINE AND PROCESSES FOR PREPARING SAME

BACKGROUND OF THE INVENTION

The background to this invention U.S. Pat. No. 3,313,813 patented Apr. 11, 1967 and issued to Edward J. Cragoe, Jr., shows novel (3-amino-5,6-disubstituted-pyrazinoyl)guanidine compounds. The compounds of the U.S. Pat. No. 3,313,813 are useful because they possess diuretic and natriuretic properties. They differ from most of the known, effective diuretic agents, however, in that the compounds of the U.S. Pat. No. 3,313,813 selectively enhance the excretion of sodium ions while simultaneously causing a decrease in excretion of potassium ions. The potassium loss, which is caused by known diuretics, often results in a severe muscular weakness. Since the compounds of the U.S. Pat. No. 3,313,813 prevent the potassium depletion, they have this decided advantage as diuretics. As diuretic agents, they can be used for the treatment of edema, hypertension and other diseases or conditions known to be responsive to this therapy and are especially useful when used in combination with or concomitantly with potassium losing diuretic agents.

Applicants' instant compounds shown in Formula I subsequently differ from the compounds shown in U.S. Pat. No. 3,313,813, in that they have a sulfamoylguanidino group (—N=C(NH$_2$)NH—SO$_2$NH$_2$) or substituted sulfamoylguanidino group in place of the guanidino group of the compounds in the stated U.S. Patent. Applicants have found that the sulfamoylguanidino group changes the pharmaceutical action and utility of these compounds. It has been found in U.S. Pat. No. 3,313,813 that the pyrazinoylguanidine compounds therein described when co-administered with other diuretic agents known to enhance the elimination of potassium ions along with sodium ions, will maintain the potassium ion excretion at approximately the normal or control rate and thus overcome this undesirable property of other diuretic agents.

In actuality, applicants' compounds in the instant case as further described, accomplish the objective previously achieved by using a combination of the pyrazinoylguanidine compounds of the U.S. Pat. No. 3,313,813 with diuretic agents which cause elimination of sodium with concomitant excessive potassium elimination. Thus, the effect of introducing a sulfamoyl group to the pyrazinoylguanidine compounds of the U.S. Pat. No. 3,313,813 results in producing eukalemic saluretic agents. Since the compounds of the instant invention are thus eukalemic saluretic agents they constitute single entities which are useful for the treatment of edema and hypertension and other diseases or conditions known to be responsive to this therapy.

SUMMARY OF THE INVENTION

The instant case covers novel N-pyrazinecarbonyl-N'-substituted-sulfamoyluanidines and processes for making the same. The novel compounds of this invention are depicted in Formula I below.

FORMULA I wherein
R$^1$ is hydrogen,
lower alkyl having from 1 to 5 carbon atoms such as methyl, ethyl, isopropyl, n-butyl, n-pentyl,
cycloalkyl having from 3 to 6 carbon atoms such as cyclopropyl, cyclopentyl and cyclohexyl;
lower alkenyl having from 2 to 3 carbon atoms such as allyl;
R$^2$ is hydrogen,
lower alkyl having from 1 to 5 carbon atoms such as methyl, ethyl, isopropyl and n-butyl,
R$^1$ and R$^2$ can be joined to form, with the nitrogen atom to which they are attached, a heterocyclic ring having 3 to 6 carbon atoms therein;
R$^3$ is hydrogen,
lower alkyl having from 1 to 5 carbon atoms such as methyl, ethyl, isopropyl, butyl and pentyl;
R$^4$ is hydrogen,
lower alkyl having from 1 to 5 carbon atoms such as methyl, ethyl, isopropyl, butyl, tert. butyl and n-pentyl;
cycloalkyl having from 3 to 6 nuclear carbon atoms such as cyclopropyl, cyclopentyl and cyclohexyl;
R$^5$ is hydrogen,
lower lkyl having from 1 to 5 carbon atoms such as methyl, ethyl, isopropyl, butyl and pentyl,
cycloalkyl having from 3 to 6 nuclear carbon atoms such as cyclopropyl, cyclopentyl and cyclohexyl;
X is halo such as fluoro, chloro, bromo or iodo;
and the pharmaceutically acceptable non-toxic acid addition salts thereof.

The preferred compounds of this invention, in other words those having enhanced diuretic, saluretic activity while maintaining unchanged potassium blood levels are those compounds of Formula I wherein
R$^1$ = R$^3$ = hydrogen;
R$^2$ = R$^4$ = R$^5$ = lower alkyl having 1 to 3 carbon atoms;
X = chloro;
and the pharmaceutically acceptable non-toxic acid addition salts thereof.

The compounds of this invention as shown by Formula I an the preferred compounds discussed above are useful because they possess diuretic and natriuretic properties. In addition, they are useful eukalemic saluretics, in other words, the compounds of the instant case cause neither loss or abnormal retention of potassium ions. In contradistinction, the pyrazinoylguanidine compounds of U.S. Pat. No. 3,313,813 do cause a decrease in the excretion of potassium ions. However, other well known diuretics such as furosemide, chlorthalidone and acetazolamide cause an increase in potassium excretion which often results in muscular weakness. Applicants' compounds combine in a single agent the advantages of a combination of the known pyrazinoylguanidine diuretics of U.S. Pat. No. 3,313,813 which decrease potassium with the known diuretics which cause a potassium loss. Thus, the compounds of this invention maintain the excretion of potassium at approximately normal levels while causing an increased renal elimination of sodium ions and water which is the desirable characteristic of the diuretic.

Also covered within the scope of the above Formula I compounds and the preferred compounds are the pharmaceutically acceptable acid addition salts thereof. These salts can be made by reacting the free base with a pharmaceutically acceptable acid such as for example, hydrochloric acid, sulfuric acid, hydrobromic acid or isethionic acid. These salts, as stated above, are to be considered as included in this invention.

The products of this invention can be administered to patients (both human and animal) in the form of pills, tablets, capsules, elixirs, injectable preparations and the like. They can be administered either orally or parentally or any other feasible method as known to those skilled in the art such as intravenously or in the form of suppositories and the like.

The type of formulation to be administered can be comprised of one or more of the compounds of this invention as the only essential active ingredient of the pharmaceutical formulation. The formulations are merely combinations of the active ingredient mentioned with pharmaceutically inert carriers and the like.

The compounds of this invention are advantageously administered at a dosage range of from about 5 mg. to about one gram per day or a somewhat higher or lower dosage at the physician's discretion, preferably in subdivided amounts on a 2 to 4 times a day regimen and most preferably at a dosage range from 10 to 500 mg. per day. It will be realized by those skilled in the art that the dosage range for any particular patient (animal or human) will depend upon the severity of the disease treated, weight of the patient and any other condition which the physician or other person skilled in the art will take account of.

The compounds disclosed in this invention in Formula I and the preferred compounds can be formed according to the process described below.

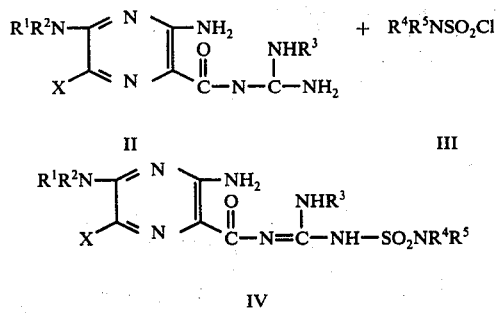

involving a reaction of pyrazinoylguanidine with a sulfamoylchloride to produce the desired product. The reaction is usually run in an inert solvent preferably a solvent such as tetrahydrofuran, dioxane, dimethoxyethane or acetonitrile at a temperature from about room temperature to the reflux temperature (particularly the reflux temperature) of the particular solvent used. The reaction time is usually from one to 48 hours and the reactants are in mole to mole ratios. None of these reaction conditions are critical and they can be varied by those skilled in the art.

All the starting materials used in the process described above are shown in and disclosed in U.S. Pat. No. 3,313,813 mentioned previously or at least can be obviously prepared from compounds disclosed in the aforementioned patent.

Representative examples to illustrate this invention are the following:

EXAMPLE 1

3-Amino-5-isopropylamino-6-chloro-N-{[(dimethylaminosulfonyl)amino]aminomethylene}-2-pyrazinecarboxamide A solution of N-amidino-3-amino-5-isopropylamino-6-chloro-2-pyrazinecarboxamide (13.9 g., 0.05 mole) and dimethylsulfamoyl chloride (7.2 g., 0.05 mole) in tetrahydrofuran (200 ml.) is refluxed for two hours. The solvent is distilled to a volume of 30 ml. which is poured into toluene (200 ml.) with vigorous stirring. A solid is filtered and the toluene is evaporated to a viscous yellow oil which upon trituration with isopropanol affords 3-amino-5-isopropylamino-6-chloro-N-{[(dimethylaminosulfonyl)amino]aminomethylene}-2-pyrazinecarboxamide which melts at 172° C. after recrystallization from isopropanol.

Analysis for $C_{11}H_{19}ClN_8O_3S$; Calc.: C, 34.87; H, 5.06; N, 29.58; Found: C, 34.99; H, 4.81; N, 29.23.

EXAMPLE 2

By following substantially the procedure described in Example 1 but substituting for the N-amidino-3-amino-5-isopropylamino-6-chloro-2-pyrazinecarboxamide an equimolar amount of the compounds shown in List 1 below there is obtained an equivalent amount of the respective compounds shown in List 2 below.

List 1

N-amidino-3-amino-5-methylamino-6-chloro-2-pyrazinecarboxamide;
N-amidino-3-amino-5-ethylamino-6-chloro-2-pyrazinecarboxamide;
N-amidino-3-amino-5-propylamino-6-chloro-2-pyrazinecarboxamide;
N-amidino-3-amino-5-butylamino-6-chloro-2-pyrazinecarboxamide;
N-amidino-3-amino-5-dimethylamino-6-chloro-2-pyrazinecarboxamide;
N-amidino-3-amino-5-diethylamino-6-chloro-2-pyrazinecarboxamide;
N-amidino-3-amino-5-cyclopentylamino-6-chloro-2-pyrazinecarboxamide;
N-amidino-3-amino-5-cyclohexylamino-6-chloro-2-pyrazinecarboxamide;
N-amidino-3-amino-5-pyrrolidino-6-chloro-2-pyrazinecarboxamide;
N-amidino-3-amino-5-piperidino-6-chloro-2-pyrazinecarboxamide;

List 2

3-amino-5-methylamino-6-chloro-N-{[(dimethylaminosulfonyl)amino]aminomethylene}-2-pyrazinecarboxamide;
3-amino-5-ethylamino-6-chloro-N-{[(dimethylaminosulfonyl)amino]aminomethylene}-2-pyrazinecarboxamide;
3-amino-5-propylamino-6-chloro-N-{[(dimethylaminosulfonyl)amino]aminomethylene}-2-pyrazinecarboxamide;
3-amino-5-butylamino-6-chloro-N-{[(dimethylaminosulfonyl)amino]aminomethylene}-2-pyrazinecarboxamide;
3-amino-5-dimethylamino-6-chloro-N{[(dimethylaminosulfonyl)amino]aminomethylene}-2-pyrazinecarboxamide;

3-amino-5-diethylamino-6-chloro-N-{[(dimethylaminosulfonyl)amino]aminomethylene}-2-pyrazinecarboxamide;
3-amino-5-cyclopentylamino-6-chloro-N-{[(dimethylaminosulfonyl)amino]aminomethylene}-2-pyrazinecarboxamide;
3-amino-5-cyclohexylamino-6-chloro-N{[(dimethylaminosulfonyl)amino]aminomethylene}-2-pyrazinecarboxamide;
3-amino-5-pyrrolidino-6-chloro-N-{[(dimethylaminosulfonyl)amino]aminomethylene}-2-pyrazinecarboxamide;
3-amino-5-piperidino-6-chloro-N-{[(dimethylaminosulfonyl)amino]aminomethylene}-2-pyrazinecarboxamide.

EXAMPLE 3

By following substantially the procedure described in Example 1 but substituting for the N-amidino-3-amino-5-isopropylamino-6-chloro-2-pyrazinecarboxamide an equimolar amount of the compounds shown in List 1 below there is obtained an equivalent amount of the respective compounds shown in List 2 below.

List 1

N-amidino-3,5-diamino-6-fluoro-2-pyrazinecarboxamide;
N-amidino-3,5-diamino-6-chloro-2-pyrazinecarboxamide;
N-amidino-3,5-diamino-6-bromo-2-pyrazinecarboxamide;
N-amidino-3,5-diamino-6-iodo-2-pyrazinecarboxamide.

List 2

3,5-diamino-6-fluoro-N-{[(dimethylaminosulfonyl)amino]aminomethylene}-2-pyrazinecarboxamide;
3,5-diamino-6-chloro-N-{[(dimethylaminosulfonyl)amino]aminomethylene}-2-pyrazinecarboxamide;
3,5-diamino-6-bromo-N-{[(dimethylaminosulfonyl)amino]aminomethylene}-2-pyrazinecarboxamide;
3,5-diamino-6-iodo-N-{[(dimethylaminosulfonyl)amino]aminomethylene}-2-pyrazinecarboxamide.

EXAMPLE 4

By following substantially the procedure described in Example 1 but substituting for the dimethylsulfamoyl chloride therein described an equimolar amount of the compounds shown in List 1 below there is obtained an equivalent amount of the respective compounds shown in List 2 below.

List 1 methylsulfamoyl chloride;
ethylsulfamoyl chloride;
propylsulfamoyl chloride;
isopropylsulfamoyl chloride;
diethylsulfamoyl chloride;
butylsulfamoyl chloride;
tert-butylsulfamoyl chloride;
cyclopentylsulfamoyl chloride;
cyclohexylsulfamoyl chloride.

List 2

3-amino-5-isopropylamino-6-chloro-N-{[(methylaminosulfonyl)amino]aminomethylene}-2-pyrazinecarboxamide;
3-amino-5-isopropylamino-6-chloro-N-{[(ethylaminosulfonyl)amino]aminomethylene}-2-pyrazinecarboxamide;
3-amino-5-isopropylamino-6-chloro-N-{[(propylaminosulfonyl)amino]aminomethylene}-2-pyrazinecarboxamide;
3-amino-5-isopropylamino-6-chloro-N-{[(isopropylaminosulfonyl)-amino]aminomethylene}-2-pyrazinecarboxamide;
3-amino-5-isopropylamino-6-chloro-N-{[(diethylaminosulfonyl)amino]aminomethylene}-2-pyrazinecarboxamide;
3-amino-5-isopropylamino-6-chloro-N-{[(butylaminosulfonyl)amino]aminomethylene}-2-pyrazinecarboxamide;
3-amino-5-isopropylamino-6-chloro-N-{[(tert-butylaminosulfonyl)-amino]aminomethylene}-2-pyrazinecarboxamide;
3-amino-5-isopropylamino-6-chloro-N-{[(cyclopentylaminosulfonyl)amino]aminomethylene}-2-pyrazinecarboxamide;
3-amino-5-isopropylamino-6-chloro-N-{[(cyclohexylaminosulfonyl)amino]aminomethylene}-2-pyrazinecarboxamide.

What is claimed is:

1. A compound of the formula:

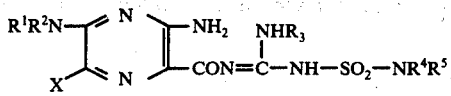

wherein
R$^1$ is hydrogen,
  lower alkyl having from 1 to 5 carbon atoms;
  cycloalkyl having from 3 to 6 carbon atoms,
  lower alkenyl having from 2 to 3 carbon atoms;
R$^2$ is hydrogen,
  lower alkyl having 1 to 5 carbon atoms;
R$^1$ and R$^2$ can be joined to form with the nitrogen atom to which they are attached a heterocyclic ring having 3 to 6 carbon atoms therein;
R$^3$ is hydrogen,
  lower alkyl having from 1 to 5 carbon atoms;
R$^4$ is hydrogen,
  lower alkyl having from 1 to 5 carbon atoms,
  cycloalkyl having from 3 to 6 nuclear carbon atoms;
R$^5$ is hydrogen,
  lower alkyl having 1 to 5 carbon atoms,
  cycloalkyl having from 3 to 6 nuclear carbon atoms;
X is halogen;
and the pharmaceutically acceptable non-toxic acid addition salts thereof.

2. A compound of the formula:

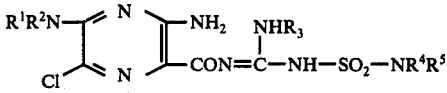

wherein
R$^1$ and R$^3$ are hydrogen;
R$^2$, R$^4$ and R$^5$ are lower alkyl having from 1 to 3 carbon atoms;
and the pharmaceutically acceptable non-toxic acid addition salts thereof.

3. A compound of claim 2 wherein
$R^1$ and $R^3$ are hydrogen;
$R^2$ is isopropyl;
$R^4$ and $R^5$ are methyl;
which is 3-amino-5-isopropylamino-6-chloro-N-{[(dimethylaminosulfonyl)aminomethylene]}-2-pyrazinecarboxamide.

4. A method of treating edema which comprises administering to a patient a pharmacologically acceptable dose of a compound of the formula:

$$R^1R^2N-\underset{X}{\overset{N}{\diagup}}\underset{N}{\overset{}{\diagdown}}\underset{CON=C-NH-SO_2-NR^4R^5}{\overset{NH_2\quad NHR_3}{}}$$

wherein
$R^1$ is hydrogen,
  lower alkyl having from 1 to 5 carbon atoms;
  cycloalkyl having from 3 to 6 carbon atoms,
  lower alkenyl having from 2 to 3 carbon atoms;
$R^2$ is hydrogen,
  lower alkyl having 1 to 5 carbon atoms;
$R^1$ and $R^2$ can be joined to form with the nitrogen atom to which they are attached a heterocyclic ring having 3 to 6 carbon atoms therein;
$R^3$ is hydrogen,
  lower alkyl having from 1 to 5 carbon atoms;
$R^4$ is hydrogen,
  lower alkyl having from 1 to 5 carbon atoms,
  cycloalkyl having from 3 to 6 nuclear carbon atoms;
$R^5$ is hydrogen,
  lower alkyl having 1 to 5 carbon atoms,
  cycloalkyl having from 3 to 6 nuclear carbon atoms;
X is halogen;
and the pharmaceutically acceptable non-toxic acid addition salts thereof.

5. A method of treating edema which consists essentially of administering to a patient in need of such treatment a unit dosage of from 5 mg. to 1 gm./day of a compound of the formula:

$$R^1R^2N-\underset{Cl}{\overset{N}{\diagup}}\underset{N}{\overset{}{\diagdown}}\underset{CON=C-NH-SO_2-NR^4R^5}{\overset{NH_2\quad NHR_3}{}}$$

wherein
$R^1$ and $R^3$ are hydrogen;
$R^2$, $R^4$ and $R^5$ are lower alkyl having from 1 to 3 carbon atoms;
and the pharmaceutically acceptable non-toxic acid addition salts thereof.

* * * * *